(12) United States Patent
Mooty et al.

(10) Patent No.: US 8,166,797 B2
(45) Date of Patent: May 1, 2012

(54) GUNFIRE SHOCK SIMULATOR AND METHOD OF USING SAME

(75) Inventors: Gregory G. Mooty, Austin, TX (US);
James E. Fitzpatrick, Austin, TX (US);
Timothy D. Honker, Austin, TX (US);
Phillip J. Izzi, Round Rock, TX (US);
Eric C. Segerstrom, Austin, TX (US)

(73) Assignee: Ascendant Engineering Solutions, LLC, Austin, TX (US)

( * ) Notice: Subject to any disclaimer, the term of this patent is extended or adjusted under 35 U.S.C. 154(b) by 270 days.

(21) Appl. No.: 12/658,132

(22) Filed: Feb. 3, 2010

(65) Prior Publication Data

US 2010/0199745 A1 Aug. 12, 2010

Related U.S. Application Data

(60) Provisional application No. 61/207,042, filed on Feb. 6, 2009.

(51) Int. Cl.
*G01M 7/00* (2006.01)
(52) U.S. Cl. ...................................... 73/12.11
(58) Field of Classification Search ....... 73/12.01–12.14
See application file for complete search history.

(56) References Cited

U.S. PATENT DOCUMENTS

| | | | |
|---|---|---|---|
| 2,554,714 A | 5/1951 | McPherren | |
| 3,693,432 A | 9/1972 | Stewart | |
| 4,050,166 A | 9/1977 | Swiatosz | |
| 4,079,525 A | 3/1978 | Linton | |
| 4,302,190 A | 11/1981 | Shaw | |
| 4,349,200 A * | 9/1982 | Wakefield | 273/371 |
| 4,380,437 A | 4/1983 | Yarborough | |
| 4,416,630 A | 11/1983 | Hagen | |
| 4,480,999 A | 11/1984 | Witherell | |
| 4,495,792 A * | 1/1985 | Bai et al. | 73/12.06 |
| 4,682,490 A | 7/1987 | Adelman | |
| 4,686,886 A | 8/1987 | Caserza | |
| 5,003,811 A | 4/1991 | Shannon | |
| 5,402,678 A | 4/1995 | Fritz | |
| 5,565,626 A | 10/1996 | Davie | |
| 5,857,854 A | 1/1999 | Kwalwasser | |
| 6,634,209 B1 * | 10/2003 | Kastendieck et al. | 73/12.07 |
| 7,159,478 B2 | 1/2007 | Schubert | |
| 2003/0073056 A1 * | 4/2003 | Kim | 434/16 |
| 2005/0074726 A1 | 4/2005 | Metcalfe | |
| 2006/0027225 A1 | 2/2006 | Homsky | |
| 2007/0275354 A1 | 11/2007 | Beckmann | |
| 2008/0131848 A1 | 6/2008 | Wilson | |

* cited by examiner

*Primary Examiner* — Max Noori
(74) *Attorney, Agent, or Firm* — David O. Simmons

(57) ABSTRACT

A gunfire shock simulation apparatus that uses an actual firearm for generating and measuring shock response data without a pyrotechnic discharge. The apparatus exerts an impact on a discharge end of a barrel of the firearm for simulating the pyrotechnic discharge event of a round of ammunition discharged within the firearm. Following such impact, the apparatus cycles a bolt carrier group of the firearm for simulating movement of the bolt carrier group resulting from the pyrotechnic discharge event of a round of ammunition. A sensing device is used for gathering shock response data in three perpendicular reference axes. By adjusting the manner in which the impact is applied to the discharge end of the barrel and/or the manner in which the bolt carrier group is cycled, resulting shock response data can be tuned to closely approximate that generated by live fire of the firearm.

25 Claims, 10 Drawing Sheets

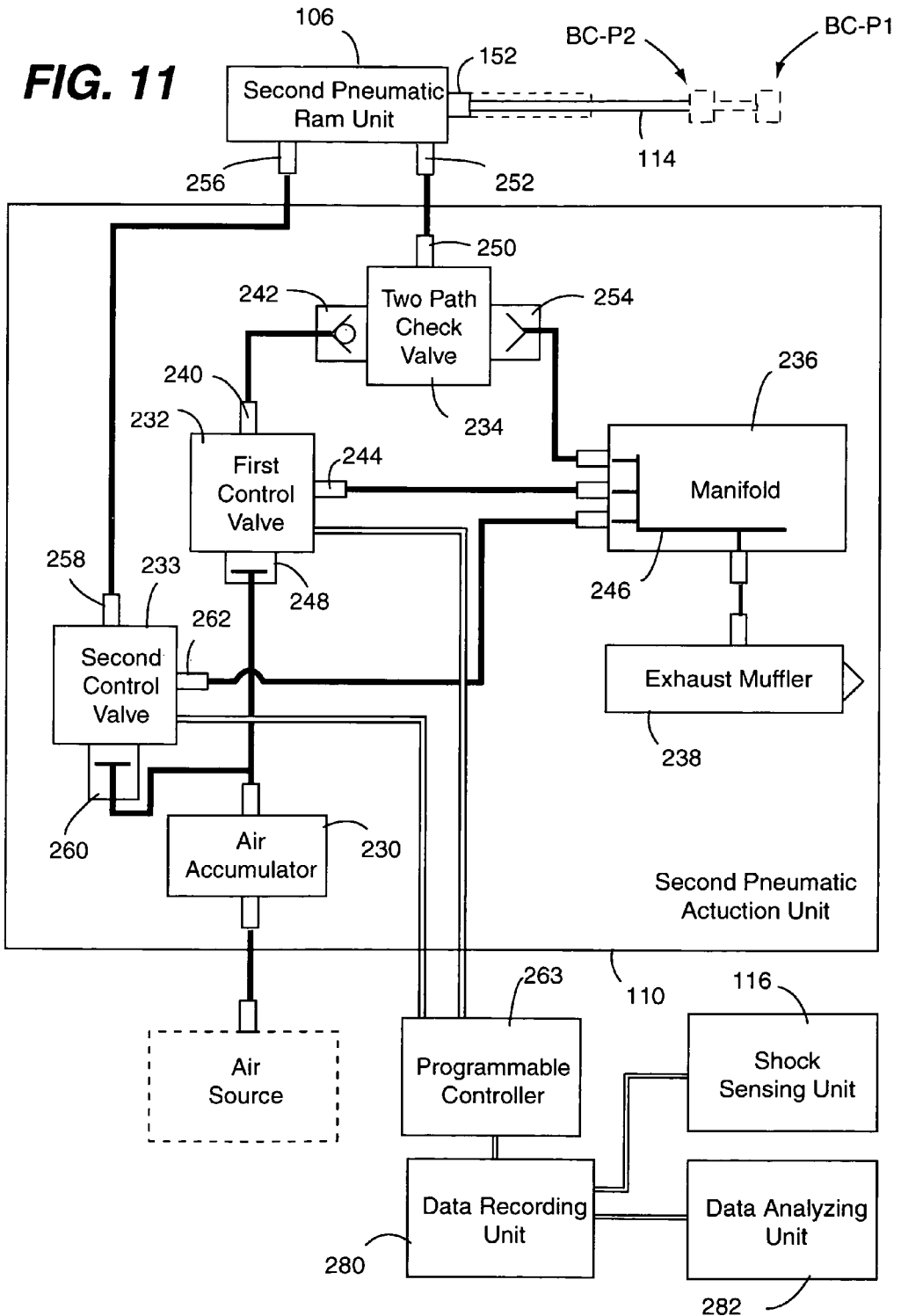

GUNFIRE SHOCK SIMULATOR AND METHOD OF USING SAME

CROSS REFERENCE TO RELATED APPLICATIONS

This patent application claims priority from U.S. Provisional Patent Application having Ser. No. 61/207,042; filed Feb. 6, 2009; entitled "Gunfire Shock Simulator And Method For Analyzing Data Acquired Therefrom"; having a common applicant herewith; and being incorporated herein in its entirety by reference.

FIELD OF THE DISCLOSURE

The disclosures made herein relate generally to apparatuses configured for simulating shock in an article or system and, more particularly, to apparatuses configured for simulating gunfire shock events resulting from pyrotechnic discharge in a weapon (e.g., a firearm).

BACKGROUND

Testing of weapon sights has required either actual firing on a real weapon, or use of drop shock machines or impact producing machines coupled to vibration slip plates and/or electrodynamic shakers. Live fire testing is expensive, time consuming and requires very specialized facilities. Drop shock machines and electrodynamic shakers are expensive and only available in specialized environmental test laboratories. Furthermore, neither of these methods can adequately reproduce specific shock time histories of pyrotechnic discharge, nor can they produce them at the high cyclic rate of fire (e.g., as high as approximately 700-950 rounds per minute) that are characteristic of a pyrotechnic energized weapon operating in full-auto mode.

The gunfire shock of a pyrotechnic energized weapon that uses energy provided by discharge of a pyrotechnic charge to energize action of a bolt carrier assembly (e.g., an M16/AR15/M4 weapon) consists of two shock pulses. FIG. 1 shows a typical longitudinal shock time history graph 10 for one set of live fire gunfire shock events in such a weapon. Longitudinal refers to shocks along an axis extending substantially parallel to a longitudinal axis of the weapon's barrel. The impulse of the first of the two shock pulses (i.e., the first shock pulse 12) is in a net rearward direction, and the impulse of the second shock pulses (i.e., the second shock pulse 14) is in a net forward direction with respect to the sight orientation. The first shock pulse 12 is due to the actual pyrotechnic shock event of cartridge (i.e., pyrotechnic) ignition and the impulse of the bullet (i.e., projectile) accelerating out of the weapon's barrel. The second shock pulse 14 is due to the inertial translation, impact and locking of the bolt carrier group into the weapon's barrel extension as the next round is chambered (i.e., bolt open/closure shock events).

Therefore, an apparatus that simulates (e.g., nearly duplicates or closely approximates) a shock time history of a weapon without requiring discharge of a pyrotechnic for doing so overcomes drawbacks associated with conventional approaches for testing and analyzing weapon shock resulting from pyrotechnic discharge and associated operation of mechanical components of the weapon (e.g., a bolt carrier assembly), thereby making such apparatus advantageous, desirable and useful.

SUMMARY OF THE DISCLOSURE

A gunfire shock simulator (GSS) configured in accordance with the present invention is a device for simulating gunfire shock, which his useful for testing reliability and operation of a weapon and/or accessories attached thereto. In one example, such a GSS is configured for testing optical sighting devices (e.g., scopes, thermal weapon sights, laser aiming devices and the like) in combination with a weapon (e.g., a rifle in the family of M16/AR15/M4 rifles). In which case, the GSS is configured for reproducing essentially the same shock profile resulting from discharge of a pyrotechnic cartridge in the weapon under test and transmitted to an accessory sighting device mounted thereon. The GSS will also operate at approximately the same shock (firing) rate as live fire operation of the weapon when operating in full auto mode (e.g., up to about 300 rounds per minute). Accordingly, a GSS configured in accordance with the present invention will enable weapon sights designed for the weapon under test to be quickly tested (i.e., subjected to gunfire shocks) in a controlled laboratory environment without the need for actual live fire of the weapon.

As will be appreciated through the disclosures made herein, a GSS configured in accordance with the present invention addresses and/or solves previous test limitations associated with live fire testing. It allows quick testing of weapon sights on equipment that can be used in almost any environment where readily available laboratory utilities (e.g., one or more types of electrical power, compressed air source, etc) are available. Furthermore, it can allow operation at temperature extremes when used in conjunction with an environmental temperature test chamber. Lastly, when combined with the correct test equipment, it can allow for quick, in situ, bore sight retention measurements.

In preferred embodiments, a GSS configured in accordance with the present invention uses parts of an actual weapon for which gunfire shock is being simulated (e.g., an upper receiver body and barrel) in combination with pneumatic and/or electromechanical actuators to duplicate the shock profiles and/or shock response spectrums exhibited by live fire of the actual weapon. In one specific embodiment, the GSS utilizes most of a complete flat top upper receiver/barrel assembly (e.g., of a M16/AR15/M4 rifle) coupled to a buffer tube assembly (receiver extension). An accessory item unit under test (e.g., an optical sight, a thermal weapon sight) is mounted to the weapon (e.g., via an accessory mount such as a picatinny rail). A shock sensing apparatus (e.g., one or more accelerometers) can also be attached to the weapon. In this manner, the GSS serves as a surrogate for a real weapon (e.g., an M4 rifle) to impose the same shocks to sight(s) (e.g., optical sight, thermal sight, etc) used on this class of weapon. Furthermore, it serves to duplicate as close as possible not only the shock levels, but also the mass and stiffness reflective of a corresponding real weapon. Additionally, it reproduces the shocks at approximately the same round per minute firing rate (e.g., up to about 300 rounds per minute) as the live fire firing rate of the weapon when firing in full-auto mode.

In one embodiment of the present invention, an apparatus for simulating live fire shock response in a weapon comprises a chassis, a first shock imparting device, a second shock imparting device, a first actuation unit, and a second actuation unit. The chassis includes a frame, one or more mounting structures fixedly engagable with a receiver body of the weapon, and on or more vibration attenuation structures coupling the one or more mounting structures to the frame. The first shock imparting device is mounted on the frame at the first region of the frame and has a weapon engaging structure selectively moveable along a translation axis thereof. The second shock imparting device is mounted on the frame at the second region of the frame and has a weapon engaging structure selectively moveable along a translation axis thereof. The first actuation unit is coupled to the first shock imparting device. The first actuation unit provides a signal to the first shock imparting device for causing the weapon engaging structure thereof to move along the translation axis thereof from an at-rest position thereof in a direction toward the second region end portion of the frame. The second actuation unit is coupled to the second shock imparting device. The second actuation unit provides a first signal to the second shock imparting device for causing the weapon engaging structure thereof to move along the translation axis thereof from an at-rest position thereof in a direction toward the first region of the frame and, after the first signal is provided, provides a second signal to the second shock imparting device for causing the weapon engaging structure thereof to move along the translation axis thereof toward the at-rest position thereof.

In another embodiment of the present invention, an apparatus for simulating live fire shock response in a firearm comprises a firearm, a chassis, a pneumatic ram unit, and a pneumatic actuation unit. The firearm includes a receiver body and a barrel structure connected to a first end portion of the receiver body. The chassis includes a frame and a set of vibration attenuation structures coupled between the receiver body and the frame. The pneumatic ram unit is mounted on the frame adjacent a first end portion of the frame. The pneumatic ram unit includes a ram selectively moveable along a translation axis thereof and has a firearm impinging structure mounted on an end portion of the ram. The pneumatic actuation unit is coupled to the pneumatic ram unit. The pneumatic actuation unit provides compressed air to the pneumatic ram unit for causing the ram thereof to move along the translation axis thereof in a direction toward a second end portion of the frame such that the firearm impinging structure moves from an at-rest position thereof and comes into contact with the barrel structure.

In another embodiment of the present invention, an apparatus for simulating live fire shock response in a firearm comprises a firearm, a chassis, a first pneumatic ram unit, a linkage member, a second pneumatic ram unit, a first pneumatic actuation unit, and a second pneumatic actuation unit. The firearm includes a receiver body, a barrel structure connected to a first end portion of the receiver body, a receiver extension extending from a second end portion of the receiver body, a bolt carrier group slideably mounted within a central passage of the receiver body, and an action spring within a central passage of the receiver extension and constrained between an end portion of the receiver extension and a bolt carrier of the bolt carrier group. The chassis includes a frame, a first set of vibration attenuation structures coupled between the receiver body and the frame, and a second set of vibration attenuation structures coupled between the receiver extension and the frame. The first pneumatic ram unit is mounted on the frame adjacent a first end portion of the frame. The first pneumatic ram unit includes a ram selectively moveable along a translation axis thereof and has a firearm impinging structure mounted on an end portion of the ram. The linkage member is coupled at a first end portion thereof to the bolt carrier through an opening in the receiver body. The second pneumatic ram unit is mounted on the frame adjacent a second end portion of the frame. The second pneumatic ram unit includes a ram selectively moveable along a translation axis thereof and has a second end portion of the linkage member engaged therewith. The first pneumatic actuation unit is coupled to the first pneumatic ram unit. The first pneumatic actuation unit provides compressed air to the first pneumatic ram unit for causing the ram thereof to move along the translation axis thereof in a direction toward the second end portion of the frame such that the firearm impinging structure moves from an at-rest position thereof and comes into contact with the barrel structure. The second pneumatic actuation unit is coupled to the second pneumatic ram unit. The second pneumatic actuation unit provides a first signal to the second pneumatic ram unit for causing the ram thereof to move along the translation axis thereof in a direction toward the second end portion of the frame thereby engaging the linkage member with the bolt carrier such that the bolt carrier translates via ram imparted force from an at-rest position thereof in the direction toward the second end portion of the frame thereby compressing the action spring. The second pneumatic actuation unit provides a second signal to the second pneumatic ram unit after the first signal is provided and before movement of the bolt carrier induced by force from the second pneumatic ram unit is fully arrested by the action spring for causing the linkage member to become disengaged from the bolt carrier as the ram thereof moves along the translation axis thereof in a direction toward the at-rest position thereof.

In another embodiment of the present invention, a method for simulating live fire shock response in a firearm begins with an operation being performed for mounting a firearm on a gunfire shock simulation apparatus. Mounting the firearm on the gunfire shock simulation apparatus includes coupling a receiver structure of the firearm to a frame of the gunfire shock simulation apparatus through a vibration attenuation structure configured for attenuating vibration in three perpendicular axes. A centerline longitudinal axis of a barrel of the firearm extends substantially parallel with a first one of the three perpendicular axes, a second one of the three perpendicular axes extends substantially perpendicular to the first one of the three perpendicular axes, and a third one of the three perpendicular axes extends substantially perpendicular to the first and second ones of the three perpendicular axes. After mounting the firearm, an operation is performed for causing a translating structure of a first shock imparting device to strike an impingement structure fixedly attached to a projectile discharge end portion of the barrel of the firearm. After a first period of time elapses following the first shock imparting device striking the impingement structure, a translating structure of a second shock imparting device performs an operation for causing a bolt carrier group slideably mounted within a central passage of the receiver body to move via force imparted by the second shock imparting device from an at-rest position in which a bolt of the bolt carrier group is lockedly engaged with the barrel to a displaced position at which the movement of the bolt carrier group induced by force from the second shock imparting device is fully arrested by an action spring of the firearm. In conjunction with causing the translating structure of the first shock imparting device to strike the impingement structure, an operation is performed for recording a current instance of shock response data in the firearm resulting from the translating structure of the first shock imparting device striking the impingement structure and from the translating structure of the second shock imparting device causing the movement of the bolt carrier group. Thereafter, an operation is performed for comparing the current instance of the recorded shock response data to shock response data recorded during live fire of the firearm and adjusting at least one of the shock imparting devices such that a subsequent instance of the recorded shock response data exhibits less quantitative difference relative to the live fire shock response data than does the current instance of the recorded shock response data. Such adjusting is performed dependent upon quantitative differences between the current instance of the recorded shock response data and the live fire shock response data.

BRIEF DESCRIPTION OF THE DRAWINGS

FIG. 11 is a diagrammatic view showing a pneumatic circuit of a pneumatic actuation unit configured for displacing a bolt carrier in accordance with an embodiment of the present invention.

DETAILED DESCRIPTION OF THE DRAWING FIGURES

Referring to FIGS. 2-6, a gunfire shock simulator (GSS) 100 configured in accordance with an embodiment of the present invention. Advantageously, the GSS 100 is configured for providing non-pyrotechnic simulation of shock response in a weapon resulting from actual firing of a pyrotechnic charge (i.e., live fire). Furthermore, the GSS 100 reproduces specific shock time histories of pyrotechnic discharge and can produce them at the same cyclic rates of fire as during live fire (e.g., typically about 300 rounds per minute).

Figure 1:
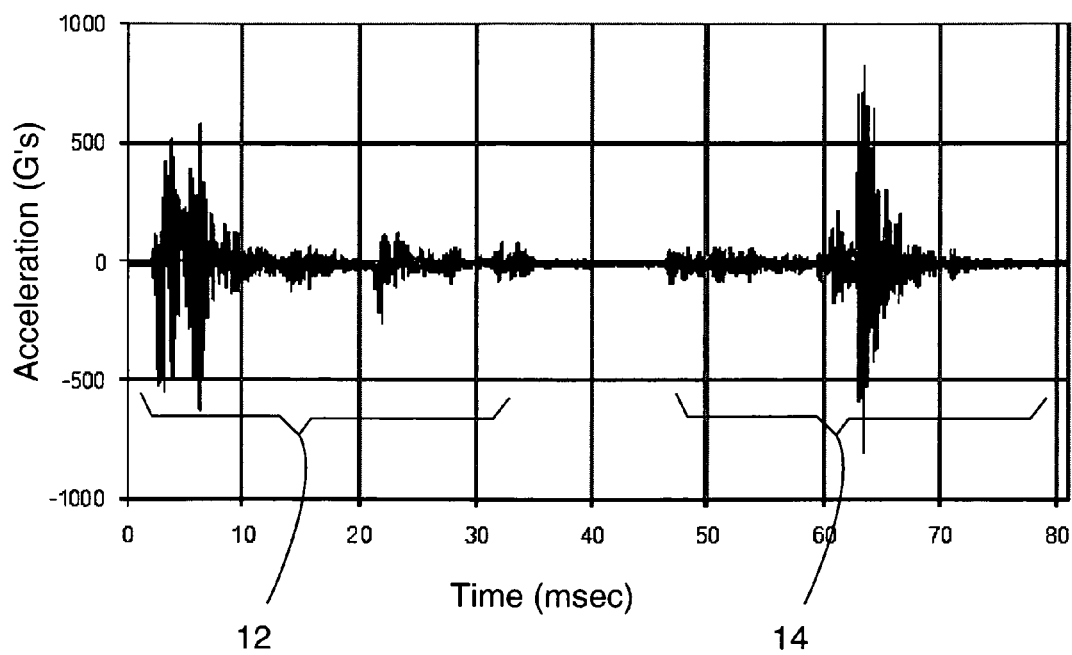
FIG. 1 is a graph showing shock time history for one set of live fire gunfire shock events in a firearm.
Figure 2:
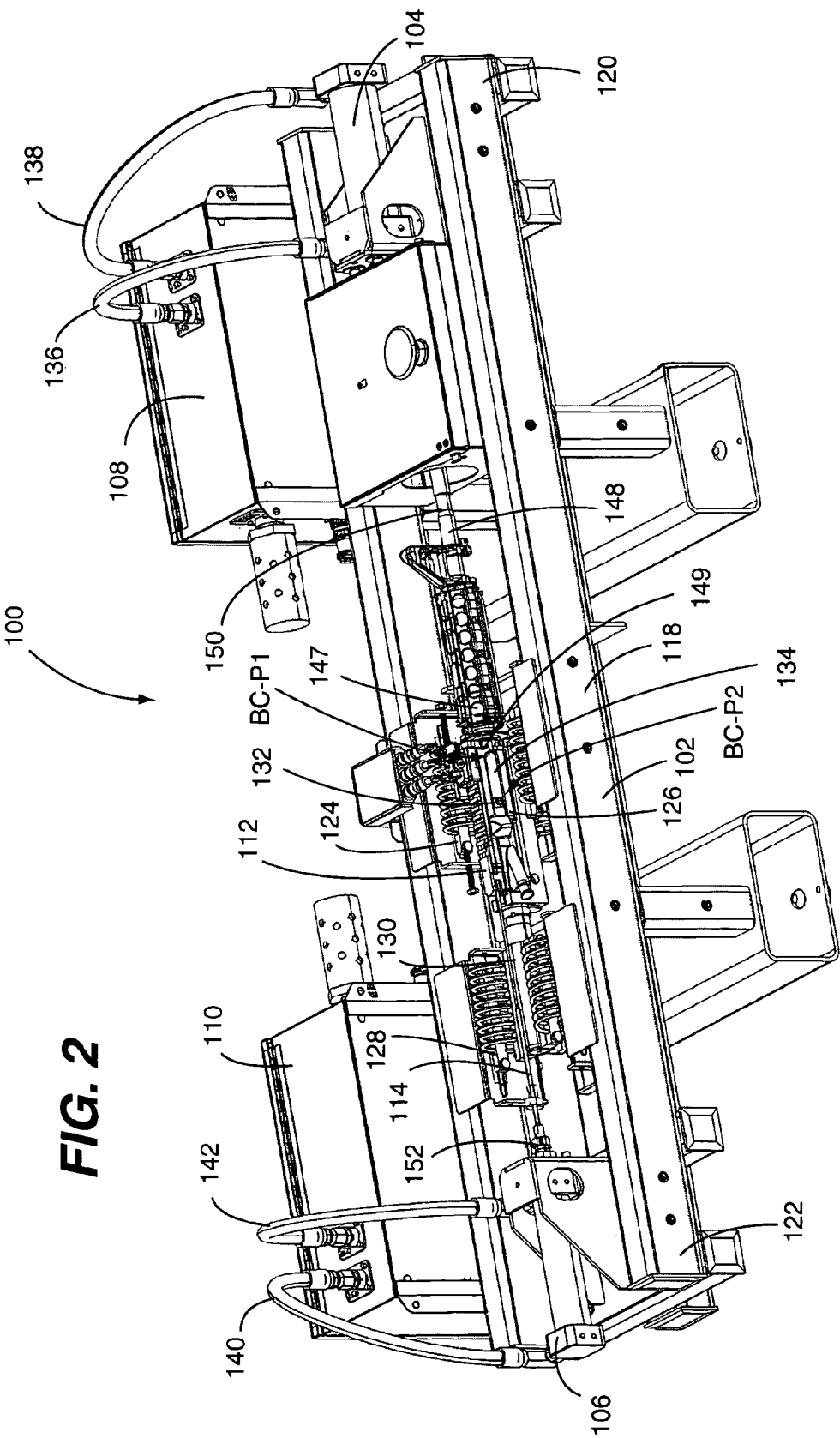
FIG. 2 is a first perspective view of a gunfire shock simulator configured in accordance with an embodiment of the present invention.
Figure 3:
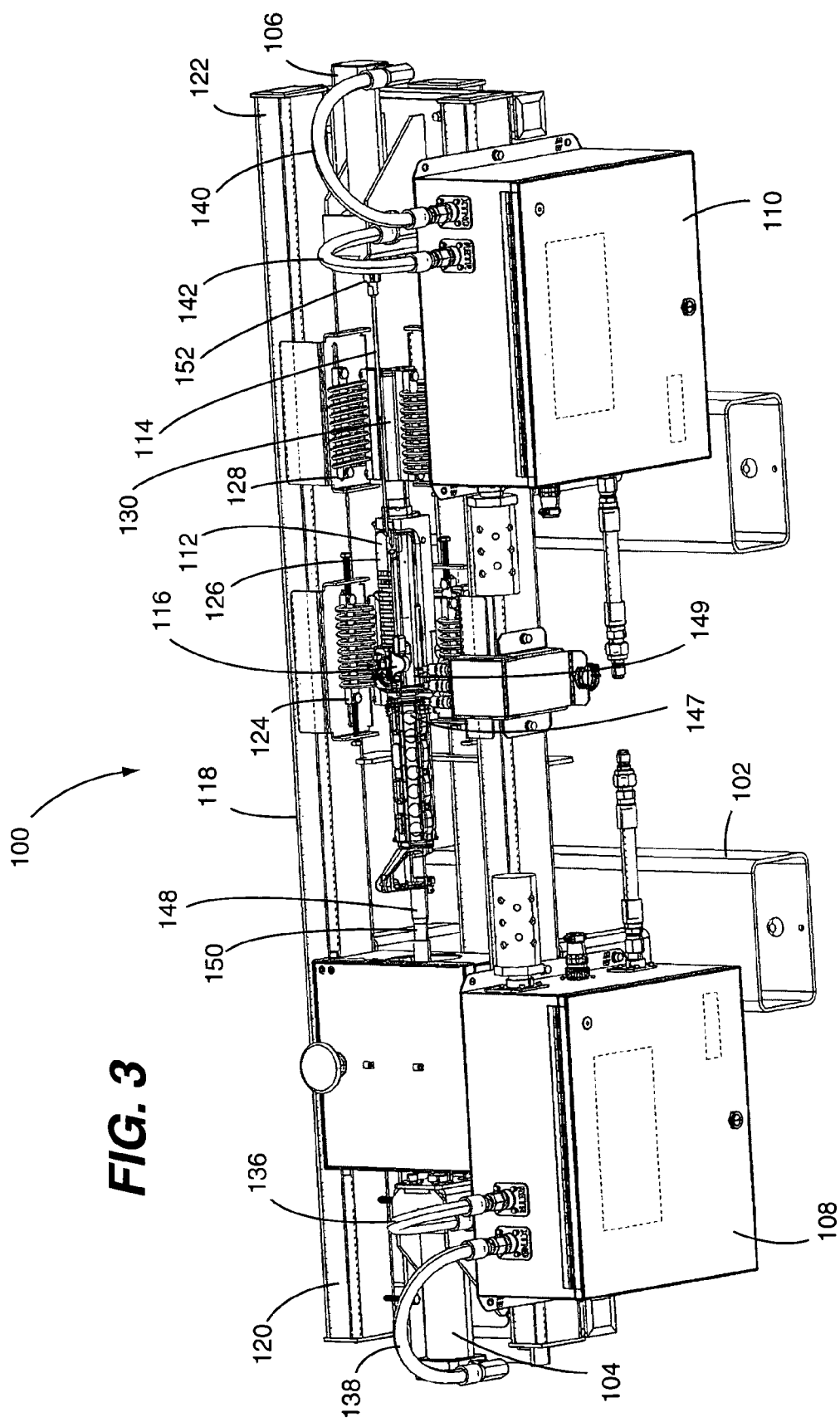
FIG. 3 is a second perspective view of the gunfire shock simulator shown in FIG. 1.
Figure 5:
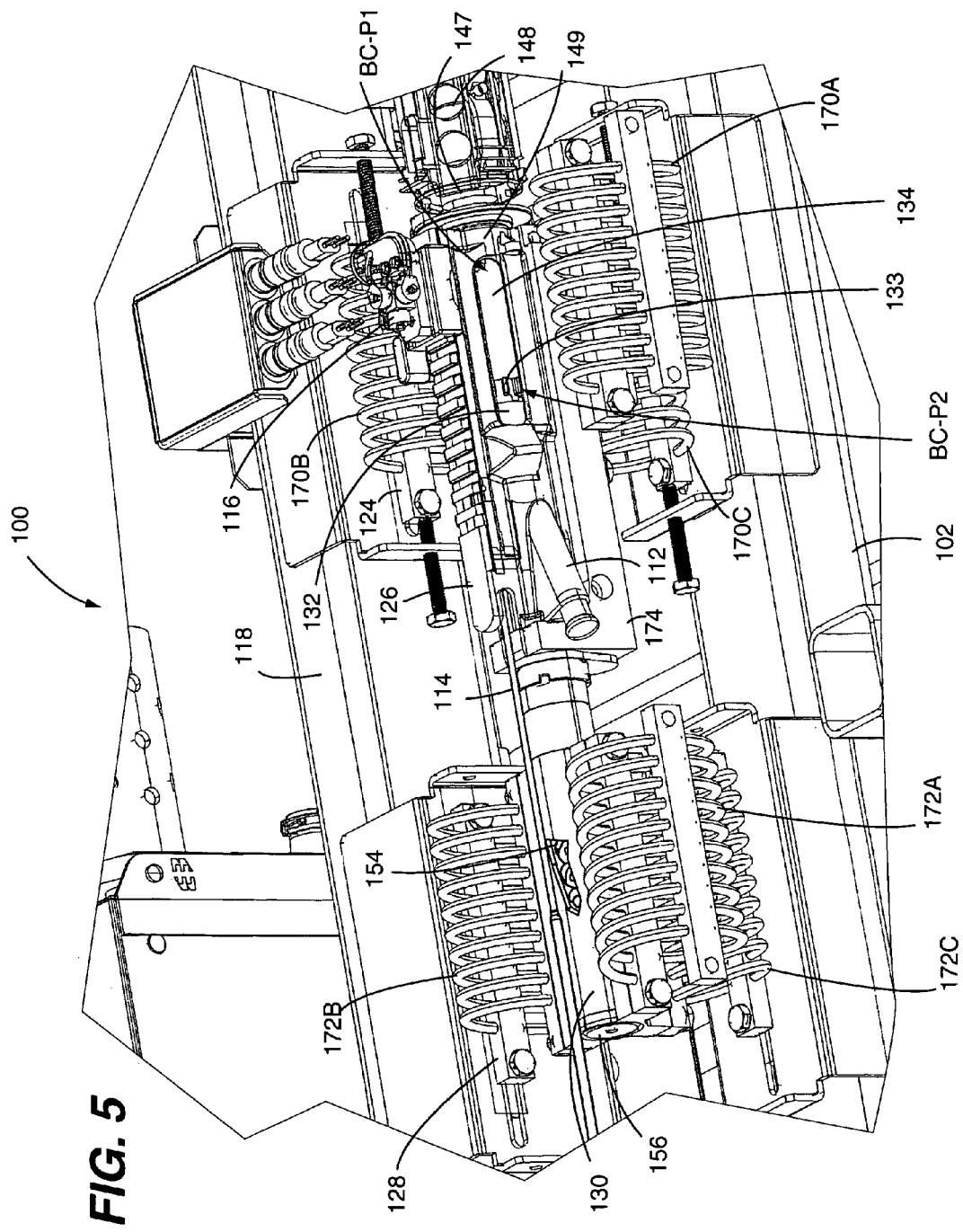
FIG. 5 is a fragmentary perspective view of the gunfire shock simulator shown in FIG. 1 showing a central portion of the gunfire shock simulator.

The GSS 100 includes a chassis 102, a first pneumatic ram unit 104, a second pneumatic ram unit 106, a first pneumatic actuation unit 108, a second pneumatic actuation unit 110, a firearm 112, a bolt carrier linkage member 114, and a shock sensing unit 116. The chassis 102 includes a frame 118 having the first pneumatic ram unit 104 and the first pneumatic actuation unit 108 mounted thereon adjacent a first end portion 120 thereof and having the second pneumatic ram unit 106 and the second pneumatic actuation unit 110 mounted thereon adjacent a second end portion 122 thereof. The chassis 102 includes a first firearm mounting structure 124 that is attached between a receiver body 126 of the firearm 112 and the frame 118 and includes a second firearm mounting structure 128 attached between a receiver extension 130 of the firearm 112 and the frame 118. As will be discussed below in greater detail, the firearm mounting structures 124, 128 are configured for providing an intended configuration of vibration attenuation between the firearm 112 and the frame 118. It is disclosed herein that a firearm as used in a GSS configured in accordance with the present invention can be less than an entire firearm (e.g., an entire firearm less original equipment manufacturer (OEM) parts such as the stock, the lower receiver, the buffer tube, etc). As best shown in FIGS. 2 and 5, the bolt carrier linkage member 114 is coupled between the second pneumatic ram unit 106 and a bolt carrier 132 slideably disposed within a slideably mounted within a central passage 134 of the receiver body 126. Preferably, the bolt carrier linkage member 114 extends through a suitably and minimally sized opening in the receiver body 126.

It is disclosed herein that the present invention is not unnecessarily limited to a frame thereof being made from any particular type or configuration of materials. Functionally, the primary functionality that a frame of a GSS configured in accordance with the present invention must provide is being a rigid platform to which other components of the GSS can be adjustably and/or fixedly mounted. More specifically, it is highly desirable for structural elements of such a frame to exhibit negligible deflection under loading from components attached thereto. To this end, in one embodiment (e.g., the frame 102 shown in FIGS. 2-6), a frame configured in accordance with the present invention can be made from discrete lengths of tubular aluminum and/or steel material that is adjoined by means such as, for example, mechanical fasteners and/or welding.

The first pneumatic ram unit 104 is coupled to the first pneumatic actuation unit 108 through a pair of pneumatic hoses 136, 138. The second pneumatic ram unit 106 is coupled to the second pneumatic actuation unit 110 through a pair of pneumatic hoses 140, 142. Pressurized air is supplied from the pneumatic actuation units 108, 110 to the respective one of the pneumatic ram unit 104, 106 for controlling operation (i.e., ram movement) of each one of the of the respective pneumatic ram units 104, 106. Accordingly, it is disclosed herein that such pressurized pulses of air act as control signals (e.g., pneumatic control signals) for the pneumatic ram units 104, 106.

The first pneumatic ram unit 104 and the first pneumatic actuation unit 108 are jointly configured for causing a firearm impinging structure 144 of the first pneumatic ram unit 104 to be selectively moved between an at-rest position FIS-P1 and a displaced position FIS-P2. The firearm impinging structure 144 is connected to a ram 145 of the first pneumatic ram unit 104. In its displaced position FIS-P2, the firearm impinging structure 144 is in contact with an impingement structure 146 of the firearm 112. The impingent body 146 is connected to a barrel 148 of the firearm 112 at a discharge end 150 thereof. The barrel 148 of the firearm 112 is connected at a first end portion 147 thereof to a first end portion 149 of the receiver body 126. In this manner, actuation of the first pneumatic ram unit 104 via the first pneumatic actuation unit 108 causes the firearm impinging structure 144 to strike the impingent body 146 for generating a shock response simulating that of actual pyrotechnic discharge and projectile acceleration.

Figure 4:
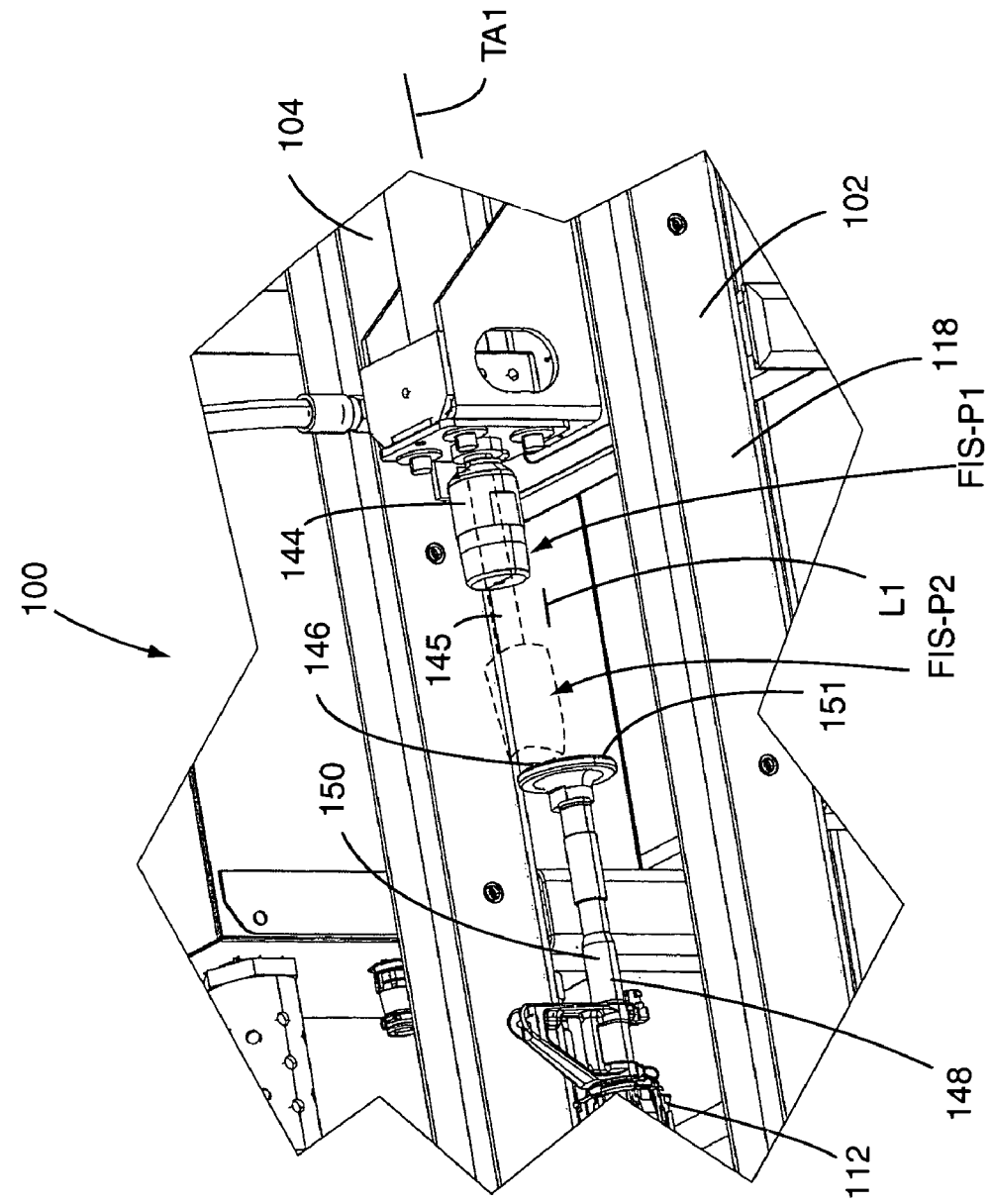
FIG. 4 is a fragmentary perspective view of the gunfire shock simulator shown, in FIG. 1 showing a first end portion of the gunfire shock simulator.

As shown in FIG. 4, the impingement structure 146 can include a substantially flat impingement surface 151 upon which the firearm impinging structure 144 comes into contact. Such a substantially flat impingement surface 151 extends substantially perpendicular to a centerline longitudinal axis L1 of the barrel 148. A translation axis TA1 of the ram 145 of the first pneumatic ram unit 104 extends substantially parallel to the centerline longitudinal axis L1 of the barrel 148. As shown, the centerline longitudinal axis L1 of the barrel 148 and the translation axis TA1 of the ram 145 are substantially offset from each other (e.g., in one of both axes extending perpendicular to the centerline longitudinal axis L1 of the barrel 148). It is disclosed herein that such offset can be useful in altering the shock response in the firearm 112. It is also disclosed herein that adjusting the distance between the impingement structure 146 and the firearm impinging structure 144 when the ram 145 is in its at-rest position FIS-P1 can be useful in altering the shock response in the firearm 112. Accordingly, such adjustments individually and jointly allow tuning of 3-axis shock response in the firearm 112. It is also disclosed herein that the mass, material (e.g., type, harness, stiffness, density, etc) and/or contact surface profile of the firearm impingement structure 144 can be altered to allow tuning of 3-axis shock response in the firearm 112.

Figure 6:
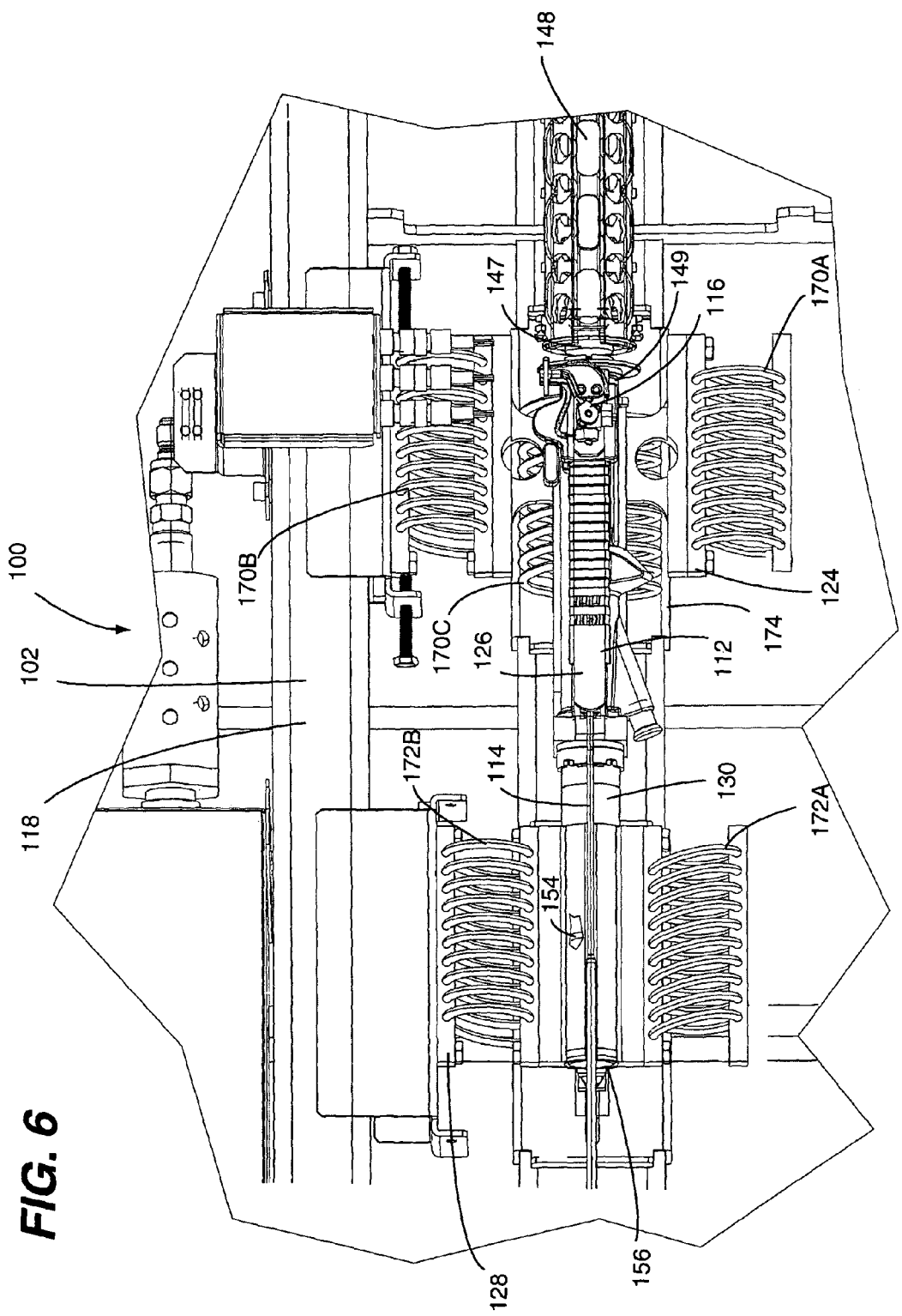
FIG. 6 is a fragmentary top view of the gunfire shock simulator shown in FIG. 1 showing the central portion of the gunfire shock simulator.

Referring to FIGS. 5 and 6, the second ram unit 106 and the second pneumatic actuation unit 110 are jointly configured for causing the bolt carrier 132 to be selectively moved from an at-rest position BC-P1 toward a displaced position BC-P2. For clarification, it is disclosed herein that a bolt 133 of the bolt carrier 132 (i.e., jointly part of a bolt carrier group) is lockedly engaged with bolt lugs of the barrel 148 when the bolt carrier 132 is in its at-rest position BC-P1 and that movement of the bolt carrier towards its a displaced position BC-P2 causes the bolt 133 to become unlocked from engagement with the bolt lugs at the first end portion 149 of the receiver body 126. The bolt carrier 132 is connected to a ram 152 of the second pneumatic ram unit 106 through the bolt carrier linkage member 114. An action spring 154 is mounted within the receiver extension 130 and is constrained between an end portion 156 of the receiver extension 130 and the bolt carrier 132 for biasing the bolt carrier 132 to its at-rest position BC-P1. In this manner, actuation of the second pneumatic ram unit 106 via the second pneumatic actuation unit 110 causes the bolt carrier 132 to correspondingly cycled from its at-rest position BC-P1 (i.e., locked position) toward its fully displaced position and, under force applied by the action spring 154, back to its at-rest position BC-P1.

Figure 7:
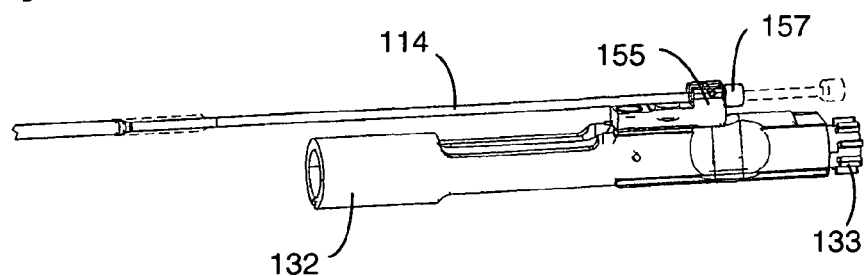
FIG. 7 is a perspective view showing interconnectivity of a bolt carrier and bolt carrier engagement member configured in accordance with an embodiment of the present invention.

Preferably, inertial movement of the bolt carrier 132 (i.e., induced by force from the second pneumatic ram unit 106) from its at-rest position BC-P1 toward its displaced position BC-P2 is initiated by the second ram unit 106 followed by such inertial movement being fully and solely arrested by the action spring 154 and then the bolt carrier 132 being urged back to its at-rest position BC-P1 under force applied only by the action spring 154. To this end, as shown in FIG. 7 the linkage member 114 can be slideably extended through a passage, channel or other suitable structure of a linkage member engaging structure 155 attached to the bolt carrier 132. In this manner, relative movement of the linkage member 114 with respect to the bolt carrier 132 in the direction toward the receiver extension 130 causes an end portion 157 of the linkage member 114 to engage (e.g., bear against) the linkage member engaging structure 155 thereby translating the bolt carrier 132 in concert with the linkage member 114. Furthermore, relative movement of the linkage member 114 with respect to the bolt carrier 132 in a direction away from the extension tube 130 causes the linkage member 114 to slide with respect to the linkage member engaging structure 155 thereby allowing the bolt carrier 132 to translate independent of the linkage member 114. Preferably, but not necessarily, the linkage member engaging structure 155 is provided at an intended position of a gas key or tappet rod lug of the bolt carrier 132.

In preferred embodiments of the present invention, shocks are generated using pneumatic devices. However, it is disclosed herein that embodiments of the present invention are not unnecessarily limited to shocks being generated using pneumatic devices. For example, it is disclosed herein that hydraulic means, electromagnetic means, electromechanical means, or other suitable known type(s) of force generating means can be used for applying forces on a firearm for generating shock response therein. Accordingly, in view of the foregoing disclosure, it can be seen that the pneumatic ram units 104, 106 are embodiments of shock imparting devices and the pneumatic actuation unit 108, 110 are each embodiments of a respective actuation unit thereof.

As best shown in FIGS. 5 and 6, the shock sensing unit 116 is rigidly mounted on the receiver body 126 (e.g., on an accessory mounting rail thereof). Advantageously, the shock sensing unit 116 can be configured for sensing shock response along three perpendicular axes. In one embodiment, translation axis of the rams 145, 152 and the centerline longitudinal axis L1 of the barrel 148 each extend substantially parallel with the first one of the three perpendicular axes. As will be discussed below in greater detail, simultaneously sensing shock response in three perpendicular axes at a common location of a receiver body of a firearm under test is advantageous in that it enables an accurate representation of live fire shock response in the firearm to be recorded and, correspondingly, enables a more close approximation of that shock response to be simulated by a GSS configured in accordance with an embodiment of the present invention 100. One example of a shock sensing unit configured in accordance with an embodiment of the present invention includes 3 single-axis Endevco brand accelerometers (P/N 7250 AM2-1) mounted a triaxial Endevco brand block (P/N 2950 M18), which is mounted on an accessory rail mount offered by LaRue Tactical as model no. LT172 Rail-Grabber.

Still referring to FIGS. 5 and 6, the firearm 112 is mounted on the frame 118 through a first set of vibration attenuation structures (i.e., the first-set vibration attenuation structures 170A, 170B, 170C) coupled between the receiver body 126 and the frame 118 and through a second set of vibration attenuation structures (i.e., the second-set vibration attenuation structures 172A, 172B, 172C) coupled between the receiver extension 130 and the frame 118. The receiver body 126 is mounted directly on a receiver body mounting structure 174. The receiver extension 130 is fixedly mounted (e.g., preferably in a manner that is substantially rigid) directly on the receiver body mounting structure 174 (e.g., in the same manner as it would be attached to a lower receiver of the firearm 112). Each one of the first-set vibration attenuation structures 170A, 170B, 170C can be independently attached between the frame 118 and the receiver body mounting structure 174. Similarly, each one of the second-set vibration attenuation structures 172A, 172B, 172C can be independently attached between the frame 118 and the receiver extension 130. In one embodiment, as shown, the receiver body 132 can be disposed between an opposing pair of vibration attenuation structures of the first set of vibration attenuation structures (i.e., vibration attenuation structures 170A, 170B) and above a third one of the first set of vibration attenuation structures (i.e., vibration attenuation structure 170C) and, similarly, the receiver extension 130 can be disposed between an opposing pair of vibration attenuation structures of the second set of vibration attenuation structures (i.e., vibration attenuation structures 172A, 172B) and above a third one of the second set of vibration attenuation structures (i.e., vibration attenuation structures 172C).

Figure 8:
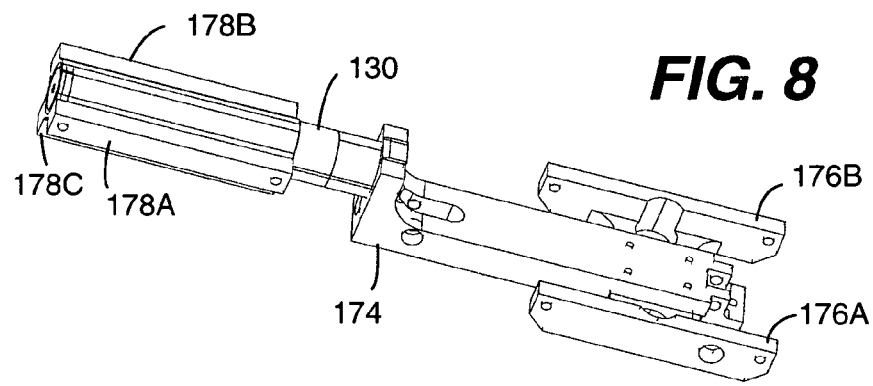
FIG. 8 is a top perspective view showing a receiver body mounting structure and interconnected receiver extension both configured in accordance with an embodiment of the present invention.
Figure 9:
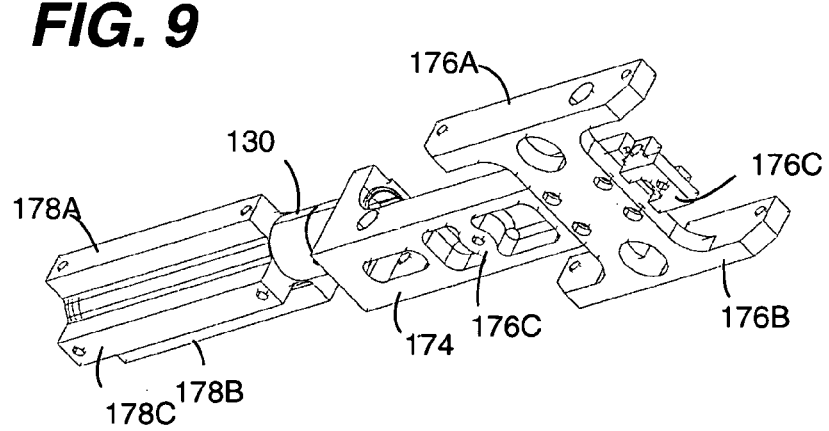
FIG. 9 is a bottom perspective view showing the receiver body mounting structure and interconnected receiver extension of FIG. 8.

As best shown in FIGS. 8 and 9, the receiver body mounting structure 174 and the receiver extension 130 are both configured for having the respective vibration attenuation structures attached thereto. The receiver body mounting structure 174 includes spaced apart attenuator mounting portions 176A, 176B and a centrally-located attenuator mounting portion 176C. The receiver extension 130 includes spaced apart attenuator mounting portions 178A, 178B and a centrally-located attenuator mounting portion 178C. Preferably, but not necessarily, the receiver body mounting structure 174 is configured for being attached to the receiver body 132 in a similar manner or same manner as an original equipment manufacturer (OEM) lower receiver body of the firearm 112 is attached to the receiver body 132. Similarly, the receiver extension 130 is preferably, but not necessarily, configured for replicating action spring functionality provided by an OEM receiver extension and for being attached to the receiver body mounting structure 174 in a similar manner or same manner as an OEM receiver extension of the firearm 112 is attached to the OEM lower receiver body thereof. Thus, it is disclosed herein that a firearm configured for used in a GSS in accordance with the present invention can include a receiver body mounting structure such as the receiver body mounting structure 174.

Preferably, an entire weight of the firearm 112 is supported on the frame 118 through only the two sets of vibration attenuation structures such that weight distribution and recoil action characteristics of the firearm 112 are approximately that of a corresponding firearm (e.g., firearm using the receiver body 132 and barrel 148) when a pyrotechnic round of ammunition is discharged therein. To this end, it is disclosed herein that the combined weight and, preferably, resulting weight distribution of the firearm 112, receiver body mounting structure 174, receiver extension 130 closely approximate that of the actual (i.e., fully operational) firearm corresponding to the firearm 112 (e.g., including any accessories under test). Similarly, it is also disclosed herein that each set of vibration attenuation structures is configured (e.g., positioned, has load carrying specification, has nominal vibration attenuation specification, etc) to support the combined weight of the firearm 112, receiver body mounting structure 174, receiver extension 130 in a manner that closely approximate the manner in which the actual firearm corresponding to the firearm 112 is supported by a person during pyrotechnic discharge of such firearm. Thus, the first and second sets of vibration attenuation structures provide load bearing functionality in combination with vibration attenuation functionality.

In one embodiment, as shown in FIGS. 2, 3, 5, and 6, each one of the first-set vibration attenuation structures 170A, 170B, 170C and each one of the second-set vibration attenuation structures 172A, 172B, 172C can be wire rope isolators. However, it is disclosed herein that other types of vibration attenuation structures can be used in place of all or a portion of the first-set vibration attenuation structures 170A, 170B, 170C and/or second-set vibration attenuation structures 172A, 172B, 172C. Accordingly, the present invention is not unnecessarily limited to any particular type or arrangement of vibration attenuation structures but preferably implemented vibration attenuation structures will preferably provide vibration attenuation functionality and load bearing functionality as described herein.

Turning now to a discussion relating to use of a GSS (gunfire shock simulation) apparatus configured in accordance with an embodiment of the present invention, use of the GSS 100 for simulating gunfire shock in the firearm 112 thereof will be presented. As is disclosed above in reference to FIGS. 2-6, the firearm 112 is coupled the frame 118 of the GSS through the first-set vibration attenuation structures 170A, 170B, 170C and through the second set vibration attenuation structures 172A, 172B, 172C. The firearm is oriented such that the centerline longitudinal axis L1 of the barrel 148 extends substantially parallel with a first perpendicular sensing axis of the shock sensing device 116. A second perpendicular sensing axis extends substantially perpendicular to the first perpendicular sensing axis a third perpendicular sensing axis extends substantially perpendicular to the first and second perpendicular sensing axes.

Referring to FIGS. 2-6, with the firearm 112 mounted on the frame 118 as discussed above, the first pneumatic actuation unit 108 provides compressed air to the first pneumatic ram unit 104 for causing the ram 145 thereof to move along its translation axis in a direction toward the second end portion 122 of the frame 118 such that the firearm impinging structure displaces from its at-rest position FIS-P1 into contact with the an impingement structure 146 (i.e., at the displaced position FIS-P2 of the firearm impinging structure 144). In synchronous conjunction with the firearm impinging structure 144 being displaced from its at-rest position FIS-P1 into contact with the impingement structure 146 at a defined duration of time following the first pneumatic actuation unit 108 providing compressed air to the first pneumatic ram unit 104, the second pneumatic actuation unit 110 provides a first signal to the second pneumatic ram unit 106 for causing compressed air to move the ram 152 of the second pneumatic ram unit 106 along its translation axis from its at-rest position in a direction toward the second end portion 122 of the frame 118 thereby engaging the bolt carrier linkage member 114 with the bolt carrier 132 such that the bolt carrier 132 translates via ram induced inertia (i.e., via ram imparted force) from its at-rest position BC-P1 in the direction toward the second end portion 122 of the frame 118. Such inertial movement results in the bolt carrier 132 compressing the action spring 154. The second pneumatic actuation unit 110 provides a second signal to the second pneumatic ram unit 106 after the first signal is provided and before inertial movement of the bolt carrier 132 is fully arrested by the action spring 154. This second signal causes compressed air to move the ram 152 of the second pneumatic ram unit 106 along its translation axis from its current displaced position in a direction away from the second end portion 122 of the frame 118 thereby disengaging the bolt carrier linkage member 114 from bolt carrier 132 such that the bolt carrier 132 can travel independent of the colt carrier linkage member 114 as the bolt carrier 132 moves back to its at-rest position BC-P1.

Figure 10:
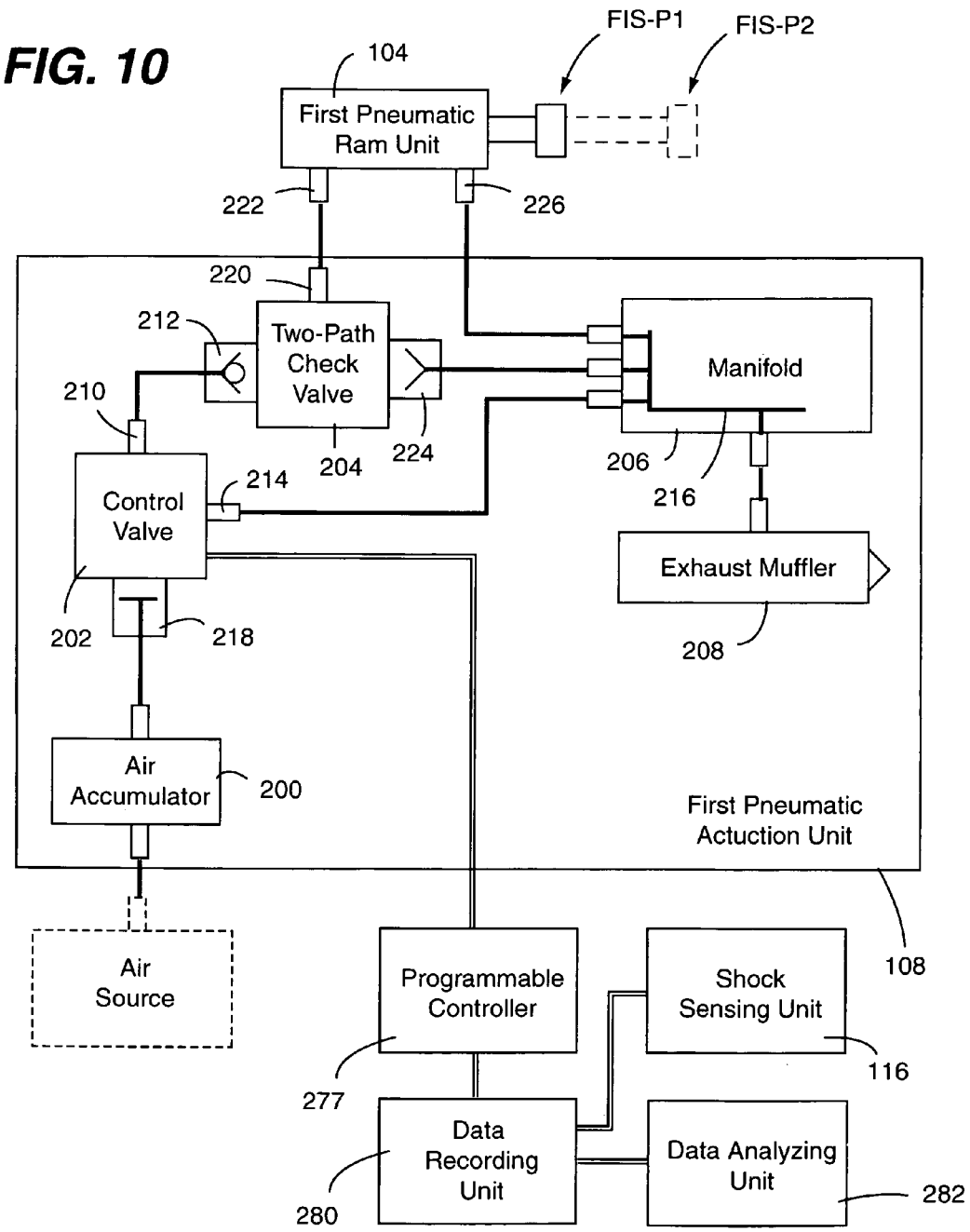
FIG. 10 is a diagrammatic view showing a pneumatic circuit of a pneumatic actuation unit configured for displacing a firearm impinging structure in accordance with an embodiment of the present invention.

FIG. 10 shows an embodiment of a pneumatic circuit of the first pneumatic actuation unit 108 suitably configured for controlling the first pneumatic ram unit 104 to cause movement of the firearm impinging structure 144 from its at-rest position FIS-P1 to its displaced position FIS-P2. The first pneumatic actuation unit 108 includes an air accumulator 200, a control valve 202, a two-path check 204, a manifold 206, and an exhaust muffler 208. A common port 210 of the control valve 202 is connected to a reverse-flow checked port 212 of the two-path check valve 204 (i.e., inhibits flow from the two-way check valve 204 to the control valve 202). A normally connected port 214 of the control valve 202 (i.e., normally connected to the common port 210) is connected to a common passage 216 of the manifold 206. A normally-disconnected port 218 of the control valve 202 (i.e., normally disconnected from the common port 210) is connected to the accumulator 200. The accumulator 200 receives compressed air from a compressed air source (e.g., shop air supply) and acts to minimizes fluctuations of air pressure within the first pneumatic actuation unit 108 that can result from cyclical operation of the control valve 202 (i.e., rapid opening and closing of the control valve 202). A common port 220 of the two-path check valve 204 is connected to a ram extending port 222 of the first pneumatic ram unit 104 (i.e., port for providing air to forcibly urge ram 145 from its at-rest position toward a displaced position thereof). A normally-connected port 224 of the two-path check valve 204 (i.e., normally-connected to the common port 220) is connected to the common passage 216 of the manifold 206. A ram retracting port 226 of the first pneumatic ram unit 104 (i.e., port for providing air to forcibly urge ram 145 from a displaced position toward its at-rest position) is connected to the common passage 216 of the manifold 206, which is connected to the exhaust muffler 208.

In operation, a programmable controller 227 (i.e., an actuation unit control apparatus) connected to the control valve 202, provides electrical control signals to the control valve 202 (e.g., a solenoid or relay thereof) at a prescribed frequency for causing compressed air to be selectively provided to the first pneumatic ram unit 104 via the two-path check valve 204 at the same frequency. In this manner, the ram 145 of the first pneumatic ram unit 104 causes the firearm impinging structure 144 to translates at the same frequency.

When a control signal (i.e., electrical energy that energizes the control valve 202) is applied to the control valve 202, the common port 210 of the control valve 202 and normally-disconnected port 218 of the control valve 202 become connected such that compressed air flows to the reverse-flow checked port 212 of the two-path check valve 204, which causes the reverse-flow checked port 212 of the two-path check valve 204 to become connected to the common port 220 of the two-path check valve 204 thereby resulting in the compressed air to be provided to the first pneumatic ram unit 104 via the ram extending port 222. As a result, the ram 145 of the first pneumatic ram unit 104 translates the firearm impinging structure 144 from its at-rest position FIS-P1 to its displaced position FIS-P2. The signal is applied for a prescribed duration of time (e.g., fractions of a second) such that the associated supply of compressed air is exerted through the control valve 202 for a similar duration of time. In one embodiment (shown), the ram 145 is biased to its at-rest position by a spring (not shown) internal to the first pneumatic ram unit 104. Accordingly, when the electrical control signal to the control valve 202 is discontinued, the supply of compressed air to the ram extension port 222 of the first pneumatic ram unit 104 is discontinued and the spring urges the ram 145 back to its at-rest position. In conjunction with the supply of compressed air to the first pneumatic ram unit 104 being discontinued and the ram 145 moving back to its at-rest position, the corresponding change in pressure within the two-path check valve 204 causes the reverse-flow checked port 212 to become disconnected from the common port 220 of the reverse-flow checked port 212 and for the normally-connected port 224 of the two-path check valve 204 to become connected to its common port 220. As such, connection of the ram retracting port 226 of the first pneumatic ram unit 104 to the exhaust muffler 208 through the common passage 216 of the manifold 206 provides a muffled vent path to the atmosphere thereby limiting translation-induced back-pressure within the first pneumatic ram unit 104.

FIG. 11 shows an embodiment of a pneumatic circuit of the second pneumatic actuation unit 110 suitably configured for controlling the second pneumatic ram unit 106 to cause movement of the bolt carrier 132 from its at-rest position BC-P1 toward its displaced position BC-P2. The second pneumatic actuation unit 110 includes an air accumulator 230, a first control valve 232, a second control valve 233, a two-path check 234, a manifold 236, and an exhaust muffler 238. A common port 240 of the first control valve 232 is connected to a reverse-flow checked port 242 of the two-path check valve 234 (i.e., inhibits flow from the two-way check valve 234 to the first control valve 232). A normally connected port 244 of the first control valve 232 (i.e., normally connected to the common port 240 of the first control valve 232) is connected to a common passage 246 of, the manifold 236. A normally-disconnected port 248 of the first control valve 232 (i.e., normally disconnected from the common port 240 of the first control valve 232) is connected to the accumulator 230. The accumulator 230 receives compressed air from a compressed air source (e.g., shop air supply) and acts to minimizes fluctuations of air pressure within the second pneumatic actuation unit 110 that can result from cyclical operation of the control valves 232, 233 (i.e., rapid opening and closing of the control valves 232, 233). A common port 250 of the two-path check valve 234 is connected to a ram retracting port 252 of the second pneumatic ram unit 106 (i.e., port for providing air to forcibly urge ram 152 from its at-rest position toward a displaced position). A normally-connected port 254 of the two-path check valve 234 (i.e., normally-connected to the common port 250) is connected to the common passage 246 of the manifold 236. A ram extending port 256 of the second pneumatic ram unit 106 (i.e., port for providing air to forcibly urge ram 152 from a displaced position toward its at-rest position) is connected to a common port 258 of the second control valve 233 manifold 236. A normally-disconnected port 260 of the second control valve 233 (i.e., normally disconnected from the common port 258 of the second control valve 233) is connected to the accumulator 230. A normally connected port 262 of the first control valve 232 (i.e., normally connected to the common port 258 of the second control valve 233) is connected to the common passage 246 of the manifold 236.

In operation, a programmable controller 263 connected to the control valves 232, 233 (e.g., which can be integral with the programmable controller 227 discussed above or a completely separate programmable controller) provides electrical control signals to the control valves 232, 233 (e.g., solenoids or relays thereof) at respective prescribed frequencies (e.g., the same frequency) and relative offsets (e.g., signal sent to second control valve 233 is chronologically offset from the signal sent to the first control valve 232) for causing compressed air to be synchronously provided to the second pneumatic ram unit 106 via the two-path check valve 234 and then, at a prescribed duration of time thereafter, for causing compressed air to be provided to the second pneumatic ram unit 106 directly from the second control valve 233. In this manner, the ram 152 of the second pneumatic ram unit 106, via the bolt carrier linkage 114, causes the bolt carrier 132 to translate from its at-rest position (e.g., adjacent the at-rest position BC-P1 of the bolt carrier 132) toward a displaced position (e.g., adjacent the displaced position BC-P2 of the bolt carrier 132) and then back to its at-rest position. In contrast to movement of the ram 145 of the first pneumatic ram unit 104, the ram 152 of the second pneumatic ram unit 106 is preferably, but not necessarily, forcibly urged by compressed air in both directions of translation.

When the programmable controller 263 applies a first control signal (i.e., electrical energy that energizes the first control valve 232) to the first control valve 232, the common port 240 of the first control valve 232 and normally-disconnected port 248 of the first control valve 232 become connected such that compressed air flows to the reverse-flow checked port 242 of the two-path check valve 234, which causes the reverse-flow checked port 232 of the two-path check valve 234 to become connected to the common port 250 of the two-path check valve 234. As a result, compressed air is provided to the second pneumatic ram unit 106 via the ram retracting port 252 such that the ram 152 of the second pneumatic ram unit 106, via the bolt carrier linkage member 114, translates the bolt carrier 132 from its at-rest position BC-P1 toward its displaced position BC-P2. During such retraction, connection of the ram extending port 256 of the second pneumatic ram unit 106 to the exhaust muffler 238 through the common passage 246 of the manifold 236 provides a muffled vent path to the atmosphere thereby limiting translation-induced back-pressure within the second pneumatic ram unit 106.

The first control signal is applied for a prescribed duration of time (e.g., fractions of a second) such that the associated supply of compressed air is exerted through the second control valve 232 for a similar duration of time. Accordingly, when the first electrical control signal is discontinued from the first control valve 232, the supply of compressed air to the ram retraction port 252 of the second pneumatic ram unit 104 is discontinued. As a result of the supply of compressed air to the ram retraction port 252 of the second pneumatic ram unit 106 being discontinued, the corresponding change in pressure within the two-path check valve 234 causes the reverse-flow checked port 242 to become disconnected from the common port 250 of the reverse-flow checked port 212 and for the normally-connected port 254 of the two path check valve 234 to become connected to its common port 250. As such, during extension of the ram 152, connection of the ram extending port 256 of the second pneumatic ram unit 106 to the exhaust muffler 238 through the common passage 246 of the manifold 236 provides a muffled vent path to the atmosphere thereby limiting translation-induced back-pressure within the second pneumatic ram unit 106.

Prior to or after the first electrical control signal being terminated, the programmable controller 263 provides a second electrical control signal to the second control valve 233 for causing the normally-disconnected port 260 of the second control valve 233 to become connected to the common port 258 of the second control valve 233. As a result, compressed air is provided from the second control valve 233 to the ram extension port 256 of the second pneumatic ram unit 106, thereby urging the ram 152 of the second pneumatic actuation unit 110. Through such sequencing of the electrical control signals to the control valves of the first and second pneumatic actuation units 108, 110, the firearm impinging structure displaces from its at-rest position FIS-P1 into contact with the impingement structure 146 thereby setting up a shock response spectrum simulating pyrotechnic discharge in the firearm 112 and, in synchronous conjunction therewith, the bolt carrier 132 is cycled for creating a shock response spectrum simulating the bolt carrier being cycled by energy derived from the pyrotechnic discharge (e.g., via energy exerted on the bolt carrier 132 via gas pressure or force from a tappet rod).

It is disclosed herein that a gunfire shock simulator in accordance with the present invention is not unnecessarily limited to a particular pneumatic control circuit configuration. For example, it is disclosed herein that a pneumatic circuit including no check values can be implemented and still provide required control of the shock imparting device (s). It is also disclosed herein that interconnection of the first and second control valves 232, 233 in FIG. 11 can be reconfigured such that the opposite ports of the second ram unit 106 are connected thereto and still provide required control of the second pneumatic ram unit 106. Thus, the depicted pneumatic circuits are presented as exemplary embodiments of a pneumatic circuit configured in accordance with the present invention.

In combination with activation of the ram actuation units 108, 110, a data recording unit 280 records a current instance of shock response data in the firearm 112 as sensed by the shock response sensing unit 116. To this end, the data recording unit 280 is suitably connected to the shock response sensing unit 116. The recorded data corresponds to the shock resulting from the firearm impinging structure 144 striking the impingement structure 146 of the barrel 148 and to the shock resulting from the bolt carrier 132 being cycled from its at-rest position BC-P1 to its displaced position BC-P2 and back to its at-rest position BC-P1. Thereafter, an operation is performed by a data analysis unit 282 for comparing the current instance of the recorded shock response data to shock response data recorded during live fire of the firearm followed, if necessary, by an operation being performed for adjusting positional parameters and/or control parameters of one or both of the shock imparting devices (e.g., first pneumatic ram unit 104 and/or the second pneumatic ram unit 106) such that a subsequent instance of recorded shock response data exhibits less quantitative difference relative to the live fire shock response data than does the current instance of the recorded shock response data. Preferably, such adjusting is performed dependent upon quantitative differences between the current instance of the recorded shock response data and the live fire shock response data. Such adjusting can include, for example, repositioning one or both of the pneumatic ram units 104, 106 along any one of the aforementioned perpendicular axes, adjusting timing at which the pneumatic actuation units 108, 110 actuate the respective one of the pneumatic ram units 104, 106, and/or adjusting the amount of air pressure provided to one or both of the pneumatic actuation units 108, 110. Accordingly, it is disclosed herein that the intent of such adjusting is at least partially intended to alter a position at which the impingement structure 146 is contacted by the firearm impinging structure 144, to alter a velocity at which the firearm impinging structure 144 strikes the impingement structure 146, to alter a momentum with which the firearm impinging structure 144 strikes the impingement structure 146, to alter the magnitude of force exerted on and/or inertia imparted upon the bolt carrier 132 by the second ram unit 106, and/or to alter translation axis angle of one or both of the pneumatic ram units 104, 106 with respect to the centerline longitudinal axis LA1 of the barrel 148. It is disclosed herein that such comparison between the current instance of the recorded shock response data to shock response data recorded during live fire of the firearm can be performed manually and/or using suitably configured instructions (e.g., software) running on a data processing apparatus (e.g., computer system). One example of a data analysis unit configured in accordance with the present invention includes data acquisition firmware comprising a firmware mounting chassis offered by National Instruments (e.g., model NI cDAQ-9172) in combination with data analysis software offered by National Instruments (e.g., LabVIEW) with signal acquisition module offered by National instruments (NI9243)

Figure 12A:
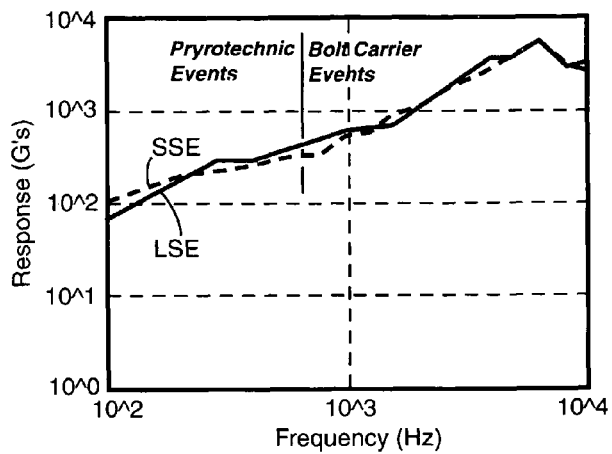
FIG. 12A is a graph showing shock response spectrum averages for simulated and live fire shock events (i.e., pyrotechnic discharge event and bolt open/closure event) for a firearm of a gunfire shock simulator configured in accordance with the present invention, wherein the shock response spectrum averages correspond to shock response in a direction extending substantially parallel to a centerline longitudinal axis of the firearm.
Figure 12B:
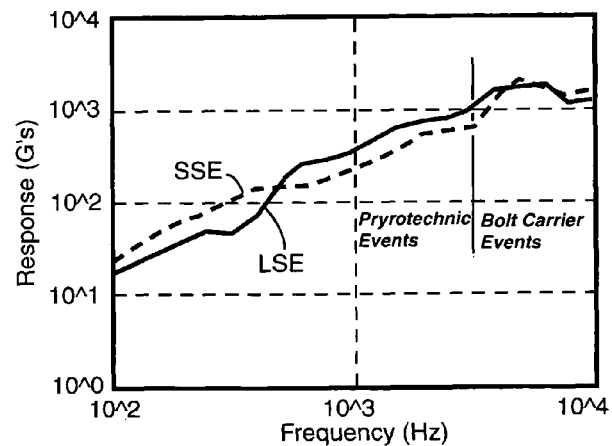
FIG. 12B is a graph showing shock response spectrum averages for simulated and live fire shock events (i.e., pyrotechnic discharge event and bolt open/closure event) for the firearm and gunfire shock simulator referred to in FIG. 12A, wherein the shock response spectrum averages correspond to shock response in a direction extending laterally perpendicular to centerline longitudinal axis of firearm).
Figure 12C:
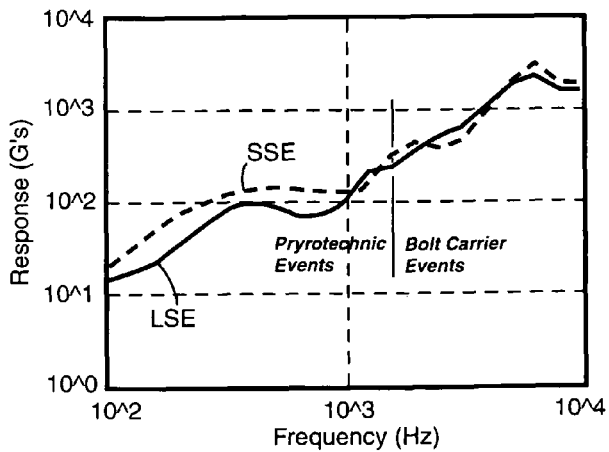
FIG. 12C is a graph showing shock response spectrum averages for simulated and live fire shock events (i.e., pyrotechnic discharge event and bolt open/closure event) for the firearm and gunfire shock simulator referred to in FIG. 12A, wherein the shock response spectrum averages correspond to shock response in a direction extending vertically perpendicular to centerline longitudinal axis of firearm).

FIGS. 12A, 12B, and 12C each show shock response spectrum (SRS) averages of simulated pyrotechnic and bolt open/closure events plotted against the SRS averages of the live gunfire for a respective one of the aforementioned perpendicular axes. As shown, the SRS curves for the simulated shock events (SSE) closely match the SRS curves for live fire shock events (LSE). FIG. 12A shows the SRS averages in the longitudinal direction (i.e., centerline longitudinal axis of firearm barrel). FIG. 12B shows the SRS averages in the lateral direction (i.e., axis extending laterally perpendicular to centerline longitudinal axis of firearm barrel). FIG. 12C shows the SRS averages in the vertical direction (i.e., axis extending vertically perpendicular to centerline longitudinal axis of firearm barrel). It has been disclosed herein that a GSS configured in accordance with the present invention advantageous allows the manner in which shock events are imparted onto a firearm by shock imparting devices thereof (e.g., the first and second pneumatic ram units 104, 106) to be altered for tailoring the SRS curves for the simulated shock events (SSE) to closely match the SRS curves for live fire shock events (LSE). Thus, analysis of information contained in, derived from, and corresponding to such plotted data can be used for causing a GSS configured in accordance with the present invention to provide SRS characteristics that closely approximate that of live fire for a firearm.

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An apparatus for simulating live fire shock response in a weapon, comprising:
a chassis including a frame, at least one mounting structure fixedly engagable with a receiver body of the weapon, and at least one vibration attenuation structure coupling said at least one mounting structure to the frame;
a first shock imparting device mounted on the frame at the first region of the frame and having a weapon engaging structure selectively moveable along a translation axis thereof;
a second shock imparting device mounted on the frame at the second region of the frame and having a weapon engaging structure selectively moveable along a translation axis thereof;
a first actuation unit coupled to the first shock imparting device, wherein the first actuation unit provides a signal to the first shock imparting device for causing the weapon engaging structure thereof to move along the translation axis thereof from an at-rest position thereof in a direction toward the second region end portion of the frame; and
a second actuation unit coupled to the second shock imparting device, wherein the second actuation unit provides a first signal to the second shock imparting device for causing the weapon engaging structure thereof to move along the translation axis thereof from an at-rest position thereof in a direction toward the first region of the frame and, after the first signal is provided, provides a second signal to the second shock imparting device for causing the weapon engaging structure thereof to move along the translation axis thereof toward the at-rest position thereof.

2. The apparatus of claim 1 wherein:
said at least one vibration attenuation structure provides vibration attenuation in three perpendicular axes;
the translation axis of each one of said shock imparting devices extend substantially parallel with a first one of said three perpendicular axes;
a second one of said three perpendicular axes extends substantially perpendicular to the first one of said three perpendicular axes; and
a third one of said three perpendicular axes extends substantially perpendicular to the first and second ones of said three perpendicular axes.

3. The apparatus of claim 2 wherein said at least one vibration attenuation structure includes at least one wire rope isolator.

4. The apparatus of claim 3 wherein the first shock imparting device is adjustably attached to the frame for allowing a position of the first shock imparting device to be selectively adjustable in directions substantially parallel to each one of said three axes.

5. The apparatus of claim 2 wherein the first shock imparting device is adjustably attached to the frame for allowing a position of the first shock imparting device to be selectively adjustable in directions substantially parallel to each one of said three axes.

6. The apparatus of claim 1, further comprising:
a shock sensing unit having a mount configured for being fixedly attached to the firearm, wherein the shock sensing unit senses shock response along three perpendicular axes and wherein the translation axis of each one of said shock imparting devices extend substantially parallel with a first one of said three perpendicular axes.

7. The apparatus of claim 6 wherein said at least one vibration attenuation structure includes a plurality of wire rope isolators each providing vibration attenuation along said three perpendicular axes.

8. An apparatus for simulating live fire shock response in a firearm, comprising:
a firearm including a receiver body and a barrel structure connected to a first end portion of the receiver body;
a chassis including a frame and a set of vibration attenuation structures coupled between the receiver body and the frame;
a shock imparting device mounted on the frame adjacent a first end portion of the frame, wherein the shock imparting device includes a portion thereof selectively moveable along a translation axis thereof and has a firearm impinging structure mounted thereon;

an actuation unit coupled to the shock imparting device, wherein the actuation unit provides a signal to the shock imparting device for causing said selectively movable portion thereof to move along the translation axis thereof in a direction toward a second end portion of the frame such that the firearm impinging structure moves from an at-rest position thereof and comes into contact with the barrel structure; and a shock sensing unit fixedly attached to the receiver body, wherein the shock sensing unit senses shock response along three perpendicular axes, wherein the translation axis of the shock imparting device extend substantially parallel with a first one of said three perpendicular axes and wherein a centerline longitudinal axis of the barrel structure extends substantially parallel with the first one of said three perpendicular axes.

9. An apparatus for simulating live fire shock response in a firearm, comprising:

a firearm including a receiver body and a barrel structure connected to a first end portion of the receiver body;

a chassis including a frame and a set of vibration attenuation structures coupled between the receiver body and the frame, wherein the set of vibration attenuation structures includes a plurality of wire rope isolators each connected to the frame and having the receiver body connected therebetween;

a shock imparting device mounted on the frame adjacent a first end portion of the frame, wherein the shock imparting device includes a portion thereof selectively moveable along a translation axis thereof and has a firearm impinging structure mounted thereon; and an actuation unit coupled to the shock imparting device, wherein the actuation unit provides a signal to the shock imparting device for causing said selectively movable portion thereof to move along the translation axis thereof in a direction toward a second end portion of the frame such that the firearm impinging structure moves from an at-rest position thereof and comes into contact with the barrel structure.

10. An apparatus for simulating live fire shock response in a firearm, comprising:

a firearm including a receiver body and a barrel structure connected to a first end portion of the receiver body; wherein the barrel structure includes an impingement structure and a rifle barrel having a first end portion connected to the receiver body and a second end portion having the impingement structure fixedly attached thereto a chassis including a frame and a set of vibration attenuation structures coupled between the receiver body and the frame;

a shock imparting device mounted on the frame adjacent a first end portion of the frame, wherein the shock imparting device includes a portion thereof selectively moveable along a translation axis thereof and has a firearm impinging structure mounted thereon and wherein the impingement structure includes a substantially flat impingement surface upon which the firearm impinging structure comes into contact, and wherein said impingement surface extends substantially perpendicular to the translation axis of the shock imparting device;

an actuation unit coupled to the shock imparting device, wherein the actuation unit provides a signal to the shock imparting device for causing said selectively movable portion thereof to move along the translation axis thereof in a direction toward a second end portion of the frame such that the firearm impinging structure moves from an at-rest position thereof and comes into contact with the barrel structure.

11. The apparatus of claim 10, further comprising:

a shock sensing unit fixedly attached to the receiver body, wherein the shock sensing unit senses shock response along three perpendicular axes;

wherein the translation axis of the shock imparting device extend substantially parallel with a first one of said three perpendicular axes; and wherein a centerline longitudinal axis of the barrel structure extends substantially parallel with the first one of said three perpendicular axes.

12. The apparatus of claim 9 wherein:

the barrel structure includes an impingement structure and a rifle barrel having a first end portion connected to the receiver body and a second end portion having the impingement structure fixedly attached thereto;

the impingement structure includes a substantially flat impingement surface upon which the firearm impinging structure comes into contact; and said impingement surface extends substantially perpendicular to the translation axis of the shock imparting device.

13. An apparatus for simulating live fire shock response in a firearm, comprising:

a firearm including a receiver body, a barrel structure connected to a first end portion of the receiver body, a receiver extension extending from a second end portion of the receiver body, a bolt carrier group slideably mounted within a central passage of the receiver body, and an action spring within a central passage of the receiver extension and constrained between an end portion of the receiver extension and a bolt carrier of the bolt carrier group;

a chassis including a frame, a first set of vibration attenuation structures coupled between the receiver body and the frame, and a second set of vibration attenuation structures coupled between the receiver extension and the frame;

a first pneumatic ram unit mounted on the frame adjacent a first end portion of the frame, wherein the first pneumatic ram unit includes a ram selectively moveable along a translation axis thereof and has a firearm impinging structure mounted on an end portion of the ram;

a linkage member coupled at a first end portion thereof to the bolt carrier through an opening in the receiver body;

a second pneumatic ram unit mounted on the frame adjacent a second end portion of the frame, wherein the second pneumatic ram unit includes a ram selectively moveable along a translation axis thereof and has a second end portion of the linkage member engaged therewith;

a first pneumatic actuation unit coupled to the first pneumatic ram unit, wherein the first pneumatic actuation unit provides compressed air to the first pneumatic ram unit for causing the ram thereof to move along the translation axis thereof in a direction toward the second end portion of the frame such that the firearm impinging structure moves from an at-rest position thereof and comes into contact with the barrel structure; and a second pneumatic actuation unit coupled to the second pneumatic ram unit, wherein the second pneumatic actuation unit provides a first signal to the second pneumatic ram unit for causing the ram thereof to move along the translation axis thereof in a direction toward the second end portion of the frame thereby engaging the linkage member with the bolt carrier such that the bolt carrier translates via ram imparted force from an at-rest position thereof in the direction toward the second end portion of the frame thereby compressing the action spring and wherein the second pneumatic actuation unit provides a second signal to the second pneumatic ram unit after the first signal is provided and before said translation of the bolt carrier is fully arrested by the action spring for causing the linkage member to become disengaged from the bolt carrier as the ram thereof moves along the translation axis thereof in a direction toward the at-rest position thereof.

14. The apparatus of claim 13, further comprising:
a shock sensing unit fixedly attached to the receiver body, wherein the shock sensing unit senses shock response along three perpendicular axes, wherein the translation axis of each one of said pneumatic ram units extends substantially parallel with a first one of said three perpendicular axes and wherein a centerline longitudinal axis of the barrel structure extends substantially parallel with the first one of said three perpendicular axes.

15. The apparatus of claim 13 wherein:
the first set of vibration attenuation structures includes a first pair of wire rope isolators each connected to the frame and having the receiver body connected therebetween; and
the second set of vibration attenuation structures includes a second pair of wire rope isolators each connected to the frame and having the receiver extension connected therebetween.

16. The apparatus of claim 13 wherein:
the barrel structure includes an impingement structure and a rifle barrel having a first end portion connected to the receiver body and a second end portion having the impingement structure fixedly attached thereto;
the impingement structure includes a substantially flat impingement surface upon which the firearm impinging structure comes into contact; and
said impingement surface extends substantially perpendicular to the translation axis of the first pneumatic ram unit.

17. The apparatus of claim 13 wherein:
the linkage member slideably extends through a passage within a linkage member engaging structure attached to the bolt carrier;
the linkage member engaging structure is provided at a position of a gas key or tappet rod lug of the bolt carrier;
relative movement of the linkage member with respect to the bolt carrier in the direction toward the second end portion of the frame causes the linkage member to bear against the linkage member engaging structure thereby translating the bolt carrier in concert with the linkage member; and
relative movement of the linkage member with respect to the bolt carrier in a direction toward the first end portion of the frame causes the linkage member to slide with respect to the linkage member engaging structure thereby allowing the bolt carrier to translate independent of the linkage member.

18. The apparatus of claim 17, further comprising:
a shock sensing unit fixedly attached to the receiver body, wherein the shock sensing unit senses shock response along three perpendicular axes;
wherein the translation axis of each one of said pneumatic ram units extends substantially parallel with a first one of said three perpendicular axes; and
wherein a centerline longitudinal axis of the barrel structure extends substantially parallel with the first one of said three perpendicular axes.

19. The apparatus of claim 18 wherein:
the barrel structure includes an impingement structure and a rifle barrel having a first end portion connected to the receiver body and a second end portion having the impingement structure fixedly attached thereto;
the impingement structure includes a substantially flat impingement surface upon which the firearm impinging structure comes into contact; and
said impingement surface extends substantially perpendicular to the translation axis of the first pneumatic ram unit.

20. A method for simulating live fire shock response in a firearm, comprising:
mounting a firearm on a gunfire shock simulation apparatus, wherein mounting the firearm on the gunfire shock simulation apparatus includes coupling a receiver structure of the firearm to a frame of the gunfire shock simulation apparatus through a vibration attenuation structure configured for attenuating vibration in three perpendicular axes, wherein a centerline longitudinal axis of a barrel of the firearm extends substantially parallel with a first one of said three perpendicular axes, wherein a second one of said three perpendicular axes extends substantially perpendicular to the first one of said three perpendicular axes, and wherein a third one of said three perpendicular axes extends substantially perpendicular to the first and second ones of said three perpendicular axes;
causing a translating structure of a first shock imparting device to strike an impingement structure fixedly attached to a projectile discharge end portion of the barrel of the firearm;
after a first period of time elapses following the first shock imparting device striking the impingement structure, a translating structure of a second shock imparting device causing a bolt carrier group slideably mounted within a central passage of the receiver body to move via force imparted by the second shock imparting device from an at-rest position in which a bolt of the bolt carrier group is lockedly engaged with the barrel to a displaced position at which said force-induced movement of the bolt carrier group is fully arrested by an action spring of the firearm;
in response to causing the translating structure of the first shock imparting device to strike the impingement structure, recording a current instance of shock response data in the firearm resulting from the translating structure of the first shock imparting device striking the impingement structure and from the translating structure of the second shock imparting device causing said movement of the bolt carrier group;
comparing the current instance of said recorded shock response data to shock response data recorded during live fire of the firearm; and
adjusting at least one of said shock imparting devices such that a subsequent instance of said recorded shock response data exhibits less quantitative difference relative to said live fire shock response data than does the current instance of said recorded shock response data, wherein said adjusting is performed dependent upon quantitative differences between the current instance of said recorded shock response data and said live fire shock response data.

21. The method of claim 20, further comprising:

after a second period of time longer than the first period of time elapses and prior to said force-induced movement of the bolt carrier group being fully arrested by the action spring, the second shock imparting device causing the translating structure thereof to become decoupled from the bolt carrier group for allowing the bolt carrier group to translate toward the at-rest position thereof unimpeded by the translating structure of the second shock imparting device from the displaced position at which said force-induced movement of the bolt carrier group is fully arrested by the action spring.

22. The method of claim 20 wherein:

mounting the firearm on the gunfire shock simulation apparatus includes orienting the firearm such that a centerline longitudinal axis of the barrel extends substantially parallel with a translation axis of the first shock imparting device;

the impingement structure includes a substantially flat impingement surface;

said impingement surface extends substantially perpendicular to the translation axis of the first shock imparting device;

the translating structure of the first shock imparting device contacts an area of said impingement surface less than an entire area of said impingement surface;

causing the translating structure of the first shock imparting device to strike the impingement structure includes causing the translating structure of the first shock imparting device to strike said impingement surface at a first position thereof after translating a first distance from an at-rest position thereof; and adjusting at least one of said shock imparting devices includes at least one of adjusting the first shock imparting device such that the translating structure thereof strikes said impingement surface at a second position thereof and adjusting the first shock imparting device such that the translating structure thereof strikes said impingement surface after translating a second distance from the at-rest position thereof.

23. The method of claim 20 wherein adjusting at least one of said shock imparting devices includes at least one of altering a manner in which the translating structure of the first shock imparting device strikes the impingement structure and altering a manner in which the translating structure of the second shock imparting device causing said movement of the bolt carrier group.

24. The method of claim 23 wherein adjusting at least one of said shock imparting devices includes altering at least one of a position at which the translating structure of the first shock imparting device strikes the impingement structure and altering a velocity at which the translating structure of the first shock imparting device is traveling when it strikes the impingement structure.

25. The method of claim 23 wherein adjusting at least one of said shock imparting devices includes altering the second shock imparting device to change a magnitude of force imparted thereby on the bolt carrier group.

* * * * *